(12) United States Patent
Hu et al.

(10) Patent No.: US 6,908,758 B2
(45) Date of Patent: Jun. 21, 2005

(54) HUMAN KINASE PROTEINS AND POLYNUCLEOTIDES ENCODING THE SAME

(75) Inventors: Yi Hu, Woodlands, TX (US); Boris Nepomnichy, Houston, TX (US); Xiaoming Wang, Northbrook, IL (US); Gregory Donoho, Woodlands, TX (US); John Scoville, Houston, TX (US); D. Wade Walke, Spring, TX (US)

(73) Assignee: Lexicon Genetics Incorporated, The Woodlands, TX (US)

( * ) Notice: Subject to any disclaimer, the term of this patent is extended or adjusted under 35 U.S.C. 154(b) by 0 days.

(21) Appl. No.: 10/620,845

(22) Filed: Jul. 15, 2003

(65) Prior Publication Data

US 2004/0115693 A1 Jun. 17, 2004

Related U.S. Application Data

(63) Continuation of application No. 09/841,683, filed on Apr. 24, 2001, now Pat. No. 6,617,147.
(60) Provisional application No. 60/201,227, filed on May 1, 2000, and provisional application No. 60/199,499, filed on Apr. 25, 2000.

(51) Int. Cl.[7] ............................ C12N 1/20; C12N 9/20; C12N 15/00; C12N 5/00; C12Q 1/68
(52) U.S. Cl. ............................ 435/252.3; 435/320.1; 435/194; 435/6; 435/325; 536/23.2
(58) Field of Search ................. 536/23.2; 435/194, 435/320.1, 325, 252.3, 6

(56) References Cited

U.S. PATENT DOCUMENTS

| | | |
|---|---|---|
| 4,215,051 A | 7/1980 | Schroeder et al. |
| 4,376,110 A | 3/1983 | David et al. |
| 4,594,595 A | 6/1986 | Struckman |
| 4,631,211 A | 12/1986 | Houghten |
| 4,689,405 A | 8/1987 | Frank et al. |
| 4,713,326 A | 12/1987 | Dattagupta et al. |
| 4,873,191 A | 10/1989 | Wagner et al. |
| 4,946,778 A | 8/1990 | Ladner et al. |
| 5,252,743 A | 10/1993 | Barrett et al. |
| 5,424,186 A | 6/1995 | Fodor et al. |
| 5,445,934 A | 8/1995 | Fodor et al. |
| 5,459,127 A | 10/1995 | Felgner et al. |
| 5,556,752 A | 9/1996 | Lockhart et al. |
| 5,700,637 A | 12/1997 | Southern |
| 5,744,305 A | 4/1998 | Fodor et al. |
| 5,837,458 A | 11/1998 | Minshull et al. |
| 5,869,336 A | 2/1999 | Meyer et al. |
| 5,877,397 A | 3/1999 | Lonberg et al. |
| 5,948,767 A | 9/1999 | Scheule et al. |
| 6,075,181 A | 6/2000 | Kucherlapati et al. |
| 6,110,490 A | 8/2000 | Thierry |
| 6,150,584 A | 11/2000 | Kucherlapati et al. |

FOREIGN PATENT DOCUMENTS

| | | |
|---|---|---|
| WO | WO 00/08151 A1 | 2/2000 |
| WO | WO 00/73469 A2 | 12/2000 |
| WO | WO 01/53455 A2 | 7/2001 |
| WO | WO 01/54733 A1 | 8/2001 |

OTHER PUBLICATIONS

Carninci et al., Meth. Enzymol., 303, 19–44, 1999.*

Bird et al, 1988, "Single–Chain Antigen–Binding Proteins", Science 242:423–426.

Bitter et al, 1987, "Expression and Secretion Vectors for Yeast", Methods in Enzymology 153:516–544.

Colbere–Garapin et al, 1981, "A New Dominant Hybrid Selective Marker for Higher Eukaryotic Cells", J. Mol. Biol. 150:1–14.

Gautier et al, 1987, "α–DNA IV:α–anomeric and β–anomeric tetrathymidylates covalently linked to intercalating oxazofopyridocarbazole. Synthesis, physiochemical properties and poly (rA) binding", Nucleic Acids Research 15(16):6625–6641.

Gordon, 1989, "International Review of Cytology", 115:171–229.

Gu et al, 1994, "Deletion of a DNA Polymerase β Gene Segment in T Cells Using Cell Type–Specific Gene Targeting", Science 265:103–106.

Huse et al, 1989, "Generation of a Large Combinatorial Library of the Immunoglobulin Repertoire in Phage Lambda", Science 246:1275–1281.

Huston et al, 1988, "Protein engineering of antibody binding sites: Recovery of specific activity in an anti–digoxin single–chain Fv analogue produced in *Escherichia coli*", Proc. Natl. Acad. Sci. USA 85:5879–5883.

Inoue et al, 1987, "Sequence–dependent hydrolysis of RNA using modified oligonucleotide splints and R Nase H", FEBS Letters 215(2):327–330.

Inoue et al, 1987, "Synthesis and hybridization studies on two complementary nona(2'–O–methyl)ribonucleotides", Nucleic Acids Research 15(15):6131–6149.

Inouye & Inouye, 1985, "Up–promoter mutations in the lpp gene of *Escherichia coli*", Nucleic Acids Research 13(9):3101–3110.

Janknecht et al, 1991, "Rapid and efficient purification of native histidine–tagged protein expressed by recombinant vaccinia virus", PNAS 88:8972–8976.

Kohler & Milstein, 1975, "Continuous cultures of fused cells secreting antibody of predefined specificity", Nature 256:495–497.

(Continued)

Primary Examiner—Maryam Monshipouri

(57) ABSTRACT

Novel human polynucleotide and polypeptide sequences are disclosed that can be used in therapeutic, diagnostic, and pharmacogenomic applications.

7 Claims, No Drawings

OTHER PUBLICATIONS

Lakso et al, 1992, "Targeted oncogene activation by site–specific recombination in transgenic mice", Proc. Natl. Acad. Sci. USA 89:6232–6236.

Lavitrano et al, 1989, "Sperm Cells ad Vectors for Introducing Froeign DNA into Eggs: Genetic Transformation of Mice", Cell 57:717–723.

Lo, 1983, "Transformation by Iontophoretic Microinjection of DNA: Multiple Integrations without Tandem Insertions", Mol. & Cell. Biology 3(10):1803–1814.

Logan et al, 1984, "Adenovirus tripartite leader sequence enhances translation of mRNAs late after infection", Proc. Natl. Acad. Sci. USA 81:3655–3659.

Lowy et al, 1980, "Isolation of Transforming DNA: Cloning the Hamster aprt Gene", Cell 22:817–823.

Morrison et al, 1984, "Chimeric human antibody molecules: Mouse antigen–binding domains with human constant region domains", Proc. Natl. Acad. Sci. USA 81:6851–6855.

Mulligan & Berg, 1981, "Selection for animal cells that express the *Escherichia coli* gene coding for xanthine–guanine phosphoribosyftransferase", Proc. Natl. Acad. Sci. USA 78(4):2072–2076.

Neuberger et al, 1984, "Recombinant antibodies possessing novel effector functions", Nature 312:604–608.

Nisonoft, 1991, "Idiotypes: Concepts and Applications", J. of Immunology 147:2429–2438.

O'Hare et al, 1981, "Transformation of mouse fibroblasts to methotrexate resistance by a recombinant plasmid expressing a prokaryotic dihydrofolate reductase", Proc. Natl. Acad. Sci. USA 78(3):1527–1531.

Santerre et al, 1984, "Expression of prokaryotic genes for hygromycin B and G418 resistance as dominant–selection markers in mouse L cells", Gene 30:147–156.

Sarin et al, 1988, "Inhibition of acquired immunodeliciency syndrome virus by oligodeoxynucleoside methylphosphonates", Proc. Natl. Acad. Sci. USA 85:7448–7451.

Smith et al, 1983, "Molecular Engineering of the Autographa californica Nuclear Polyhedrosis Virus Genome: Deletion Mutations within the Polyhedrin Gene", J. Virol. 46(2):584–593.

Smithies, 1985, "Insertion of DNA sequences into the human chromosomal β–globin locus by homologous recombination", Nature 317:230–234.

Songyang et al, 1993, "SH2 Domains Recognize Specific Phosphopeptide Sequences", Cell 72:767–778.

Stein et al, 1988, "Physiochemical properties of phosphorothioate oligodeoxynucleotides", Nucleic Acids Research 16(8):3209–3221.

Szybalska & Szybalski, 1962, "Genetics of Human Cell Lines, IV. DNA–Mediated Heritable Transformation of a Biochemical Trait", Proc. Natl. Acad. Sci. USA 48:2026–2034.

Takeda et al, 1985, "Construction of chimaeric processed immunoglobulin genes containing mouse variable and human constant region sequences", Nature 314:452–454.

Thompson et al, 1989, "Germ Line Transmission and Expression of a Corrected HPRT Gene Produced by Gene Targeting in Embryonic Stem Cells", Cell 56:313–321.

Van Der Putten et al, 1985, "Efficient insertion of genes into the mouse germ line via retroviral vectors", Proc. Natl. Acad. Sci. USA 82:6148–6152.

Van Heeke et al, 1989, "Expression of Human Asparagine Synthetase in *Escherichia coli*", J. Biol. Chemistry 264(10):5503–5509.

Ward et al, 1989, "Binding activities of a repertoire of single immunoglobulin variable domains secreted from *Escherichia coli*", Nature 341:544–546.

Wigler et al, 1977, "Transfer of Purified Herpes Virus Thymidine Kinase Gene to Cultured Mouse Cells", Cell 11:223–232.

Wigler et al, 1980, "Transformation of mammalian cells with an amplifiable dominant–acting gene", Proc. Natl. Acad. Sci. USA 77(6):3567–3570.

Database EM_EST 'Online' EMBL; Accession No. AA454060, ID HSAA54060, Jun. 11, 1997, Hillier L., et al., XP002192346, abstract.

Database EM_EST 'Online' EMBL; Accession No. AW341417, Feb. 1, 2000, NCI–CGAP: XP002193080, abstract.

Database EM_HUM 'Online' EMBL; Accession No. AJ303380, Feb. 12, 2001, MUJICA A.O, et al, Homo sapiens mRNA for serine/threonine kinase 33 (STK33 gene);, XP002192355, abstract.

Mujica, A.O. et al., "A novel serine/threonine kinase gene, STK33, on human chromosome 11p15.3," Gene: An International Journal on Genes and Gnomes, Elsevier Science Publishers, Barking, GB, vol. 280, No. 1–2, Dec. 12, 2001, p. 175–181, XP004313178.

Nairn, A.C., et al., "Calcium/calmodulin dependent protein kinases," Seminars in Cancer Biology, Saunders Scientific Publications, Philadelphia, PA, vol. 5, 1994, p. 295–303, XP002097695.

International Search Report, International Application No. PCT/US01/13149, Apr. 24, 2001.

\* cited by examiner

SEQUENCE LISTING

```
<160> NUMBER OF SEQ ID NOS: 12

<210> SEQ ID NO 1
<211> LENGTH: 1545
<212> TYPE: DNA
<213> ORGANISM: homo sapiens

<400> SEQUENCE: 1
atggctgata gtggcttaga taaaaaatcc acaaaatgcc ccgactgttc atctgcttct      60
cagaaagatg tactttgtgt atgttccagc aaaacaaggg ttcctccagt tttggtggtg     120
```

```
gaaatgtcac agacatcaag cattggtagt gcagaatctt taatttcact ggagagaaaa      180
aaagaaaaaa atatcaacag agatataacc tccaggaaag atttgccctc aagaacctca      240
aatgtagaga gaaaagcatc tcagcaacaa tggggtcggg caactttac agaaggaaaa       300 gttcctcaca taaggattga aatggagct gctattgagg aaatctatac ctttggaaga       360
atattgggaa aagggagctt tggaatagtc attgaagcga cagacaagga acagaaacg       420 aagtgggcaa ttaaaaaagt gaacaaagaa aaggctggaa gctctgctgt gaagttactt      480
gaacgagagg tgaacattct gaaaagtgta aacatgaac acatcataca tctggaacaa       540
gtatttgaaa cgccaaagaa aatgtacctt gtgatggagc tttgtgagga tggagaactc      600
aaagaaattc tggataggaa agggcatttc tcagagaatg agacaaggtg gatcattcaa      660
agtctcgcat cagctatagc atatcttcac aataatgata ttgtacatag agatctgaaa      720
ctggaaaata taatggttaa aagcagtctt attgatgata caatgaaat aaacttaaac       780 ataaaggtga ctgattttgg cttagcggtg aagaagcaaa gtaggagtga agccatgctg      840
caggccacat gtgggactcc tatctatatg gcccctgaag ttatcagtgc ccacgactat      900
agccagcagt gtgacatttg gagcataggc gtcgtaatgt acatgttatt acgtggagaa      960
ccaccctttt tggcaagctc agaagagaag cttttttgagt taataagaaa aggagaacta   1020
cattttgaaa atgcagtctg gaattccata agtgactgtg ctaaaagtgt tttgaaacaa   1080
cttatgaaag tagatcctgc tcacagaatc acagctaagg aactactaga taaccagtgg   1140
ttaacaggca ataaactttc ttcggtgaga ccaaccaatg tattagagat gatgaaggaa   1200
tggaaaaata acccagaaag tgttgaggaa aacacaacag aagagaagaa taagccgtcc   1260
actgaagaaa agttgaaaag ttaccaaccc tggggaaatg tccctgatgc caattacact   1320
tcagatgaag aggaggaaaa acagtctact gcttatgaaa agcaatttcc tgcaaccagt   1380
aaggacaact ttgatatgtg cagttcaagt ttcacatcta gcaaactcct tccagctgaa   1440
atcaagggag aaatggagaa aacccctgtg actccaagcc aaggaacagc aaccaagtac   1500
cctgctaaat ccggcgccct gtccagaacc aaaaagaaac tctaa                    1545
```

<210> SEQ ID NO 2
<211> LENGTH: 514
<212> TYPE: PRT
<213> ORGANISM: homo sapiens

<400> SEQUENCE: 2

```
Met Ala Asp Ser Gly Leu Asp Lys Lys Ser Thr Lys Cys Pro Asp Cys
 1               5                  10                  15

Ser Ser Ala Ser Gln Lys Asp Val Leu Cys Val Cys Ser Ser Lys Thr
            20                  25                  30

Arg Val Pro Pro Val Leu Val Val Glu Met Ser Gln Thr Ser Ser Ile
        35                  40                  45

Gly Ser Ala Glu Ser Leu Ile Ser Leu Glu Arg Lys Lys Glu Lys Asn
    50                  55                  60

Ile Asn Arg Asp Ile Thr Ser Arg Lys Asp Leu Pro Ser Arg Thr Ser
65                  70                  75                  80

Asn Val Glu Arg Lys Ala Ser Gln Gln Gln Trp Gly Arg Gly Asn Phe
                85                  90                  95

Thr Glu Gly Lys Val Pro His Ile Arg Ile Glu Asn Gly Ala Ala Ile
            100                 105                 110

Glu Glu Ile Tyr Thr Phe Gly Arg Ile Leu Gly Lys Gly Ser Phe Gly
```

```
                    115                 120                 125
Ile Val Ile Glu Ala Thr Asp Lys Glu Thr Thr Lys Trp Ala Ile
    130                 135                 140

Lys Lys Val Asn Lys Glu Lys Ala Gly Ser Ser Ala Val Lys Leu Leu
145                 150                 155                 160

Glu Arg Glu Val Asn Ile Leu Lys Ser Val Lys His Glu His Ile Ile
                165                 170                 175

His Leu Glu Gln Val Phe Glu Thr Pro Lys Lys Met Tyr Leu Val Met
            180                 185                 190

Glu Leu Cys Glu Asp Gly Glu Leu Lys Glu Ile Leu Asp Arg Lys Gly
            195                 200                 205

His Phe Ser Glu Asn Glu Thr Arg Trp Ile Ile Gln Ser Leu Ala Ser
    210                 215                 220

Ala Ile Ala Tyr Leu His Asn Asn Asp Ile Val His Arg Asp Leu Lys
225                 230                 235                 240

Leu Glu Asn Ile Met Val Lys Ser Ser Leu Ile Asp Asp Asn Asn Glu
                245                 250                 255

Ile Asn Leu Asn Ile Lys Val Thr Asp Phe Gly Leu Ala Val Lys Lys
            260                 265                 270

Gln Ser Arg Ser Glu Ala Met Leu Gln Ala Thr Cys Gly Thr Pro Ile
        275                 280                 285

Tyr Met Ala Pro Glu Val Ile Ser Ala His Asp Tyr Ser Gln Gln Cys
    290                 295                 300

Asp Ile Trp Ser Ile Gly Val Val Met Tyr Met Leu Arg Gly Glu
305                 310                 315                 320

Pro Pro Phe Leu Ala Ser Ser Glu Glu Lys Leu Phe Glu Leu Ile Arg
                325                 330                 335

Lys Gly Glu Leu His Phe Glu Asn Ala Val Trp Asn Ser Ile Ser Asp
            340                 345                 350

Cys Ala Lys Ser Val Leu Lys Gln Leu Met Lys Val Asp Pro Ala His
        355                 360                 365

Arg Ile Thr Ala Lys Glu Leu Leu Asp Asn Gln Trp Leu Thr Gly Asn
    370                 375                 380

Lys Leu Ser Ser Val Arg Pro Thr Asn Val Leu Glu Met Met Lys Glu
385                 390                 395                 400

Trp Lys Asn Asn Pro Glu Ser Val Glu Glu Asn Thr Thr Glu Glu Lys
                405                 410                 415

Asn Lys Pro Ser Thr Glu Glu Lys Leu Lys Ser Tyr Gln Pro Trp Gly
            420                 425                 430

Asn Val Pro Asp Ala Asn Tyr Thr Ser Asp Glu Glu Glu Lys Gln
        435                 440                 445

Ser Thr Ala Tyr Glu Lys Gln Phe Pro Ala Thr Ser Lys Asp Asn Phe
    450                 455                 460

Asp Met Cys Ser Ser Phe Thr Ser Ser Lys Leu Leu Pro Ala Glu
465                 470                 475                 480

Ile Lys Gly Glu Met Glu Lys Thr Pro Val Thr Pro Ser Gln Gly Thr
                485                 490                 495

Ala Thr Lys Tyr Pro Ala Lys Ser Gly Ala Leu Ser Arg Thr Lys Lys
            500                 505                 510

Lys Leu

<210> SEQ ID NO 3
<211> LENGTH: 2001
```

<210> SEQ ID NO 3
<211> LENGTH: 2001
<212> TYPE: DNA
<213> ORGANISM: homo sapiens

<400> SEQUENCE: 3

| | | | | | |
|---|---|---|---|---|---|
| gataaacgtt | acataactag | aaagtggcag | agctgtcacg | tgtgaatatg | tgtctagtgc | 60 |
| atccttaacc | tgaggacttc | accagttcga | aattacagtt | ttcaccatca | actaccttat | 120 |
| cctttttggt | ctggttttct | tcctcaaaca | gtggaaacat | ttttaaagtt | gcttttgttg | 180 |
| cagagttaaa | caaatggctg | atagtggctt | agataaaaaa | tccacaaaat | gccccgactg | 240 |
| ttcatctgct | tctcagaaag | atgtactttg | tgtatgttcc | agcaaaacaa | gggttcctcc | 300 |
| agttttggtg | gtggaaatgt | cacagacatc | aagcattggt | agtgcagaat | ctttaatttc | 360 |
| actggagaga | aaaaagaaa | aaatatcaa | cagagatata | acctccagga | aagatttgcc | 420 |
| ctcaagaacc | tcaaatgtag | agagaaaagc | atctcagcaa | caatgggtc | ggggcaactt | 480 |
| tacagaagga | aaagttcctc | acataaggat | tgagaatgga | gctgctattg | aggaaatcta | 540 |
| tacctttgga | agaatattgg | gaaagggag | ctttggaata | gtcattgaag | cgacagacaa | 600 |
| ggaaacagaa | acgaagtggg | caattaaaaa | agtgaacaaa | gaaaaggctg | aagctctgc | 660 |
| tgtgaagtta | cttgaacgag | aggtgaacat | tctgaaaagt | gtaaaacatg | aacacatcat | 720 |
| acatctggaa | caagtatttg | aaacgccaaa | gaaaatgtac | cttgtgatgg | agctttgtga | 780 |
| ggatggagaa | ctcaaagaaa | ttctggatag | gaaagggcat | ttctcagaga | atgagacaag | 840 |
| gtggatcatt | caaagtctcg | catcagctat | agcatatctt | cacaataatg | atattgtaca | 900 |
| tagagatctg | aaactggaaa | atataatggt | taaaagcagt | cttattgatg | ataacaatga | 960 |
| aataaactta | aacataaagg | tgactgattt | tggcttagcg | gtgaagaagc | aaagtaggag | 1020 |
| tgaagccatg | ctgcaggcca | catgtgggac | tcctatctat | atggcccctg | aagttatcag | 1080 |
| tgcccacgac | tatagccagc | agtgtgacat | ttggagcata | ggcgtcgtaa | tgtacatgtt | 1140 |
| attacgtgga | gaaccaccct | ttttggcaag | ctcagaagag | aagcttttg | agttaataag | 1200 |
| aaaaggagaa | ctacatttg | aaaatgcagt | ctggaattcc | ataagtgact | gtgctaaaag | 1260 |
| tgttttgaaa | caacttatga | agtagatcc | tgctcacaga | atcacagcta | aggaactact | 1320 |
| agataaccag | tggttaacag | gcaataaact | ttcttcggtg | agaccaacca | atgtattaga | 1380 |
| gatgatgaag | gaatgaaaa | ataacccaga | agtgttgag | gaaacacaa | cagaagagaa | 1440 |
| gaataagccg | tccactgaag | aaaagttgaa | aagttaccaa | ccctgggaa | atgtccctga | 1500 |
| tgccaattac | acttcagatg | aagaggagga | aaaacagtct | actgcttatg | aaaagcaatt | 1560 |
| tcctgcaacc | agtaaggaca | actttgatat | gtgcagttca | agtttcacat | ctagcaaact | 1620 |
| ccttccagct | gaaatcaagg | gagaaatgga | gaaaccccct | gtgactccaa | gccaaggaac | 1680 |
| agcaaccaag | taccctgcta | atccggcgc | cctgtccaga | accaaaaaga | aactctaagg | 1740 |
| ttccctccag | tgttggacag | tacaaaaaca | aagctgctct | tgttagcact | ttgatgaggg | 1800 |
| ggtaggaggg | gaagaagaca | gccctatgct | gagcttgtag | ccttttagct | ccacagagcc | 1860 |
| ccgccatgtg | tttgcaccag | cttaaaattg | aagctgctta | tctccaaagc | agcataagct | 1920 |
| gcacatggca | ttaaaggaca | gccaccagta | ggcttggcag | tgggctgcag | tggaaatcaa | 1980 |
| ctcaagatgt | acacgaaggt | t | | | | 2001 |

<210> SEQ ID NO 4
<211> LENGTH: 678
<212> TYPE: DNA
<213> ORGANISM: homo sapiens -continued

```
<400> SEQUENCE: 4
atgggagcca acacttcaag aaaaccacca gtgtttgatg aaaatgaaga tgtcaacttt    60
gaccactttg aaattttgcg agccattggg aaaggcagtt ttgggaaggt ctgcattgta   120
cagaagaatg ataccaagaa gatgtacgca atgaagtaca tgaataaaca aaagtgcgtg   180
gagcgcaatg aagtgagaaa tgtcttcaag gaactccaga tcatgcaggg tctggagcac   240
cctttcctgg ttaatttgtg gtattccttc caagatgagg aagacatgtt catggtggtg   300
gacctcctgc tgggtggaga cctgcgttat cacctgcaac agaacgtcca cttcaaggaa   360
gaaacagtga agctcttcat ctgtgagctg gtcatggccc tggactacct gcagaaccag   420
cgcatcattc acagggatat gaagcctgac aatatttac ttgacgaaca tgggcacgtg    480
cacatcacag atttcaacat tgctgcgatg ctgcccaggg agacacagat taccaccatg   540
gctggcacca agccttacat ggcacctgag atgttcagct ccagaaaagg agcaggctat   600
tcctttgctg ttgactggtg gtccctggga gtgacggcat atgaactgct gagaggccgg   660
gtggcccaga acagtag                                                  678

<210> SEQ ID NO 5
<211> LENGTH: 225
<212> TYPE: PRT
<213> ORGANISM: homo sapiens

<400> SEQUENCE: 5

Met Gly Ala Asn Thr Ser Arg Lys Pro Pro Val Phe Asp Glu Asn Glu
1               5                   10                  15

Asp Val Asn Phe Asp His Phe Glu Ile Leu Arg Ala Ile Gly Lys Gly
                20                  25                  30

Ser Phe Gly Lys Val Cys Ile Val Gln Lys Asn Asp Thr Lys Lys Met
            35                  40                  45

Tyr Ala Met Lys Tyr Met Asn Lys Gln Lys Cys Val Glu Arg Asn Glu
        50                  55                  60

Val Arg Asn Val Phe Lys Glu Leu Gln Ile Met Gln Gly Leu Glu His
65                  70                  75                  80

Pro Phe Leu Val Asn Leu Trp Tyr Ser Phe Gln Asp Glu Glu Asp Met
                85                  90                  95

Phe Met Val Val Asp Leu Leu Leu Gly Gly Asp Leu Arg Tyr His Leu
                100                 105                 110

Gln Gln Asn Val His Phe Lys Glu Glu Thr Val Lys Leu Phe Ile Cys
            115                 120                 125

Glu Leu Val Met Ala Leu Asp Tyr Leu Gln Asn Gln Arg Ile Ile His
        130                 135                 140

Arg Asp Met Lys Pro Asp Asn Ile Leu Leu Asp Glu His Gly His Val
145                 150                 155                 160

His Ile Thr Asp Phe Asn Ile Ala Ala Met Leu Pro Arg Glu Thr Gln
                165                 170                 175

Ile Thr Thr Met Ala Gly Thr Lys Pro Tyr Met Ala Pro Glu Met Phe
            180                 185                 190

Ser Ser Arg Lys Gly Ala Gly Tyr Ser Phe Ala Val Asp Trp Trp Ser
        195                 200                 205

Leu Gly Val Thr Ala Tyr Glu Leu Leu Arg Gly Arg Val Ala Gln Lys
    210                 215                 220

Gln
225
```

-continued

```
<210> SEQ ID NO 6
<211> LENGTH: 711
<212> TYPE: DNA
<213> ORGANISM: homo sapiens

<400> SEQUENCE: 6
atgggagcca acacttcaag aaaaccacca gtgtttgatg aaaatgaaga tgtcaacttt      60
gaccactttg aaattttgcg agccattggg aaaggcagtt ttgggaaggt ctgcattgta     120
cagaagaatg ataccaagaa gatgtacgca atgaagtaca tgaataaaca aaagtgcgtg     180
gagcgcaatg aagtgagaaa tgtcttcaag gaactccaga tcatgcaggg tctggagcac     240
cctttcctgg ttaatttgtg gtattccttc caagatgagg aagacatgtt catggtggtg     300
gacctcctgc tgggtggaga cctgcgttat cacctgcaac agaacgtcca cttcaaggaa     360
gaaacagtga agctcttcat ctgtgagctg gtcatggccc tggactacct gcagaaccag     420
cgcatcattc acagggatat gaagcctgac aatattttac ttgacgaaca tgggcacgtg     480
cacatcacag atttcaacat tgctgcgatg ctgcccaggg agacacagat taccaccatg     540
gctggcacca agccttacat ggcacctgag atgttcagct ccagaaaagg agcaggctat     600
tcctttgctg ttgactggtg gtccctggga gtgacggcat atgaactgct gagaggccgg     660
actgtagtag catttcctct ttggttattt ttccagcaag ttctatttta g              711

<210> SEQ ID NO 7
<211> LENGTH: 236
<212> TYPE: PRT
<213> ORGANISM: homo sapiens

<400> SEQUENCE: 7

Met Gly Ala Asn Thr Ser Arg Lys Pro Pro Val Phe Asp Glu Asn Glu
1               5                   10                  15

Asp Val Asn Phe Asp His Phe Glu Ile Leu Arg Ala Ile Gly Lys Gly
                20                  25                  30

Ser Phe Gly Lys Val Cys Ile Val Gln Lys Asn Asp Thr Lys Lys Met
            35                  40                  45

Tyr Ala Met Lys Tyr Met Asn Lys Gln Lys Cys Val Glu Arg Asn Glu
        50                  55                  60

Val Arg Asn Val Phe Lys Glu Leu Gln Ile Met Gln Gly Leu Glu His
65                  70                  75                  80

Pro Phe Leu Val Asn Leu Trp Tyr Ser Phe Gln Asp Glu Glu Asp Met
                85                  90                  95

Phe Met Val Val Asp Leu Leu Leu Gly Gly Asp Leu Arg Tyr His Leu
                100                 105                 110

Gln Gln Asn Val His Phe Lys Glu Glu Thr Val Lys Leu Phe Ile Cys
            115                 120                 125

Glu Leu Val Met Ala Leu Asp Tyr Leu Gln Asn Gln Arg Ile Ile His
        130                 135                 140

Arg Asp Met Lys Pro Asp Asn Ile Leu Leu Asp Glu His Gly His Val
145                 150                 155                 160

His Ile Thr Asp Phe Asn Ile Ala Ala Met Leu Pro Arg Glu Thr Gln
                165                 170                 175

Ile Thr Thr Met Ala Gly Thr Lys Pro Tyr Met Ala Pro Glu Met Phe
                180                 185                 190

Ser Ser Arg Lys Gly Ala Gly Tyr Ser Phe Ala Val Asp Trp Trp Ser
            195                 200                 205
```

-continued

Leu Gly Val Thr Ala Tyr Glu Leu Leu Arg Gly Arg Thr Val Val Ala
       210                 215                 220

Phe Pro Leu Trp Leu Phe Phe Gln Gln Val Leu Phe
225                 230                 235

<210> SEQ ID NO 8
<211> LENGTH: 1224
<212> TYPE: DNA
<213> ORGANISM: homo sapiens

<400> SEQUENCE: 8

| | | | | | |
|---|---|---|---|---|---|
| atgggagcca | acacttcaag | aaaaccacca | gtgtttgatg | aaaatgaaga | tgtcaacttt | 60 |
| gaccactttg | aaattttgcg | agccattggg | aaaggcagtt | ttgggaaggt | ctgcattgta | 120 |
| cagaagaatg | ataccaagaa | gatgtacgca | atgaagtaca | tgaataaaca | aaagtgcgtg | 180 |
| gagcgcaatg | aagtgagaaa | tgtcttcaag | gaactccaga | tcatgcaggg | tctggagcac | 240 |
| cctttcctgg | ttaatttgtg | gtattccttc | caagatgagg | aagacatgtt | catggtggtg | 300 |
| gacctcctgc | tgggtggaga | cctgcgttat | cacctgcaac | agaacgtcca | cttcaaggaa | 360 |
| gaaacagtga | agctcttcat | ctgtgagctg | gtcatggccc | tggactacct | gcagaaccag | 420 |
| cgcatcattc | acagggatat | aaagcctgac | aatattttac | ttgacgaaca | tgggcacgtg | 480 |
| cacatcacag | atttcaacat | tgctgcgatg | ctgcccaggg | agacacagat | taccaccatg | 540 |
| gctggcacca | gccttacat | ggcacctgag | atgttcagct | ccagaaaagg | agcaggctat | 600 |
| tcctttgctg | ttgactggtg | gtccctggga | gtgacggcat | atgaactgct | gagaggccgg | 660 |
| agaccgtatc | atattcgctc | cagtacttcc | agcaaggaaa | ttgtacacac | gtttgagacg | 720 |
| actgttgtaa | cttaccccttc | tgcctggtca | caggaaatgg | tgtcacttct | aaaaagcta | 780 |
| ctcgaaccta | atccagacca | acgattttct | cagttatctg | atgtccagaa | cttcccgtat | 840 |
| atgaatgata | taaactggga | tgcagttttt | cagaagaggc | tcattccagg | tttcattcct | 900 |
| aataaaggca | ggctgaattg | tgatcctacc | tttgaacttg | aggaaatgat | tttggagtcc | 960 |
| aaacctctac | ataagaaaaa | aaagcgtctg | gcaaagaagg | agaaggatat | gaggaaatgc | 1020 |
| gattcttctc | agacatgtct | tcttcaagag | caccttgact | ctgtccagaa | ggagttcata | 1080 |
| attttcaaca | gagaaaaagt | aaacagggac | tttaacaaaa | gacaaccaaa | tctagccttg | 1140 |
| gaacaaacca | agacccaca | agtgacaaat | ggacaaatgg | acacaggact | cagtgagact | 1200 |
| tttcagacct | cgaaagtttc | ataa | | | | 1224 |

<210> SEQ ID NO 9
<211> LENGTH: 407
<212> TYPE: PRT
<213> ORGANISM: homo sapiens

<400> SEQUENCE: 9

Met Gly Ala Asn Thr Ser Arg Lys Pro Val Phe Asp Glu Asn Glu
1               5                   10                  15

Asp Val Asn Phe Asp His Phe Glu Ile Leu Arg Ala Ile Gly Lys Gly
            20                  25                  30

Ser Phe Gly Lys Val Cys Ile Val Gln Lys Asn Asp Thr Lys Lys Met
        35                  40                  45

Tyr Ala Met Lys Tyr Met Asn Lys Gln Lys Cys Val Glu Arg Asn Glu
    50                  55                  60

Val Arg Asn Val Phe Lys Glu Leu Gln Ile Met Gln Gly Leu Glu His
65                  70                  75                  80

```
Pro Phe Leu Val Asn Leu Trp Tyr Ser Phe Gln Asp Glu Glu Asp Met
                 85                  90                  95
Phe Met Val Val Asp Leu Leu Leu Gly Gly Asp Leu Arg Tyr His Leu
                100                 105                 110
Gln Gln Asn Val His Phe Lys Glu Glu Thr Val Lys Leu Phe Ile Cys
            115                 120                 125
Glu Leu Val Met Ala Leu Asp Tyr Leu Gln Asn Gln Arg Ile Ile His
        130                 135                 140
Arg Asp Met Lys Pro Asp Asn Ile Leu Leu Asp Glu His Gly His Val
145                 150                 155                 160
His Ile Thr Asp Phe Asn Ile Ala Ala Met Leu Pro Arg Glu Thr Gln
                165                 170                 175
Ile Thr Thr Met Ala Gly Thr Lys Pro Tyr Met Ala Pro Glu Met Phe
                180                 185                 190
Ser Ser Arg Lys Gly Ala Gly Tyr Ser Phe Ala Val Asp Trp Trp Ser
            195                 200                 205
Leu Gly Val Thr Ala Tyr Glu Leu Leu Arg Gly Arg Arg Pro Tyr His
        210                 215                 220
Ile Arg Ser Ser Thr Ser Ser Lys Glu Ile Val His Thr Phe Glu Thr
225                 230                 235                 240
Thr Val Val Thr Tyr Pro Ser Ala Trp Ser Gln Glu Met Val Ser Leu
                245                 250                 255
Leu Lys Lys Leu Leu Glu Pro Asn Pro Asp Gln Arg Phe Ser Gln Leu
            260                 265                 270
Ser Asp Val Gln Asn Phe Pro Tyr Met Asn Asp Ile Asn Trp Asp Ala
        275                 280                 285
Val Phe Gln Lys Arg Leu Ile Pro Gly Phe Ile Pro Asn Lys Gly Arg
        290                 295                 300
Leu Asn Cys Asp Pro Thr Phe Glu Leu Glu Glu Met Ile Leu Glu Ser
305                 310                 315                 320
Lys Pro Leu His Lys Lys Lys Arg Leu Ala Lys Lys Glu Lys Asp
                325                 330                 335
Met Arg Lys Cys Asp Ser Ser Gln Thr Cys Leu Leu Gln Glu His Leu
            340                 345                 350
Asp Ser Val Gln Lys Glu Phe Ile Ile Phe Asn Arg Glu Lys Val Asn
        355                 360                 365
Arg Asp Phe Asn Lys Arg Gln Pro Asn Leu Ala Leu Glu Gln Thr Lys
370                 375                 380
Asp Pro Gln Val Thr Asn Gly Gln Met Asp Thr Gly Leu Ser Glu Thr
385                 390                 395                 400
Phe Gln Thr Ser Lys Val Ser
                405

<210> SEQ ID NO 10
<211> LENGTH: 1191
<212> TYPE: DNA
<213> ORGANISM: homo sapiens

<400> SEQUENCE: 10
atgggagcca acacttcaag aaaaccacca gtgtttgatg aaaatgaaga tgtcaacttt      60
gaccactttg aaattttgcg agccattggg aaaggcagtt ttgggaaggt ctgcattgta     120
cagaagaatg ataccaagaa gatgtacgca atgaagtaca tgaataaaca aaagtgcgtg     180
gagcgcaatg aagtgagaaa tgtcttcaag gaactccaga tcatgcaggg tctggagcac     240
```

```
ccttccctgg ttaatttgtg gtattccttc caagatgagg aagacatgtt catggtggtg      300
gacctcctgc tgggtggaga cctgcgttat cacctgcaac agaacgtcca cttcaaggaa      360
gaaacagtga agctcttcat ctgtgagctg gtcatggccc tggactacct gcagaaccag      420
cgcatcattc acagggatat gaagcctgac aatattttac ttgacgaaca tgggcacgtg      480
cacatcacag atttcaacat tgctgcgatg ctgcccaggg agacacagat taccaccatg      540
gctggcacca agccttacat ggcacctgag atgttcagct ccagaaaagg agcaggctat      600
tcctttgctg ttgactggtg gtccctggga gtgacggcat atgaactgct gagaggccgg      660
agaccgtatc atattcgctc cagtacttcc agcaaggaaa ttgtacacac gtttgagacg      720
actgttgtaa cttacccttc tgcctggtca caggaaatgg tgtcacttct taaaaagcta      780
ctcgaaccta atccagacca cgatttctct cagttatctg atgtccagaa cttcccgtat      840
atgaatgata taaactggga tgcagttttt cagaagaggc tcattccagg tttcattcct      900
aataaaggca ggctgaattg tgatcctacc tttgaacttg aggaaatgat tttggagtcc      960
aaacctctac ataagaaaaa aaagcgtctg gcaaagaagg agaaggatat gaggaaatgc     1020
gattcttctc agacatgtct tcttcaagag caccttgact ctgtccagaa ggagttcata     1080
attttcaaca gagaaaaagt aaacagggac tttaacaaaa gacaaccaaa tctagccttg     1140
gaacaaacca agacccaca aggtgaggat ggtcagaata caacttgta a               1191
```

<210> SEQ ID NO 11
<211> LENGTH: 396
<212> TYPE: PRT
<213> ORGANISM: homo sapiens

<400> SEQUENCE: 11

```
Met Gly Ala Asn Thr Ser Arg Lys Pro Pro Val Phe Asp Glu Asn Glu
1               5                   10                  15

Asp Val Asn Phe Asp His Phe Glu Ile Leu Arg Ala Ile Gly Lys Gly
                20                  25                  30

Ser Phe Gly Lys Val Cys Ile Val Gln Lys Asn Asp Thr Lys Lys Met
            35                  40                  45

Tyr Ala Met Lys Tyr Met Asn Lys Gln Lys Cys Val Glu Arg Asn Glu
        50                  55                  60

Val Arg Asn Val Phe Lys Glu Leu Gln Ile Met Gln Gly Leu Glu His
65                  70                  75                  80

Pro Phe Leu Val Asn Leu Trp Tyr Ser Phe Gln Asp Glu Glu Asp Met
                85                  90                  95

Phe Met Val Val Asp Leu Leu Leu Gly Gly Asp Leu Arg Tyr His Leu
                100                 105                 110

Gln Gln Asn Val His Phe Lys Glu Glu Thr Val Lys Leu Phe Ile Cys
            115                 120                 125

Glu Leu Val Met Ala Leu Asp Tyr Leu Gln Asn Gln Arg Ile Ile His
        130                 135                 140

Arg Asp Met Lys Pro Asp Asn Ile Leu Leu Asp Glu His Gly His Val
145                 150                 155                 160

His Ile Thr Asp Phe Asn Ile Ala Ala Met Leu Pro Arg Glu Thr Gln
                165                 170                 175

Ile Thr Thr Met Ala Gly Thr Lys Pro Tyr Met Ala Pro Glu Met Phe
                180                 185                 190

Ser Ser Arg Lys Gly Ala Gly Tyr Ser Phe Ala Val Asp Trp Trp Ser
            195                 200                 205
```

```
Leu Gly Val Thr Ala Tyr Glu Leu Leu Arg Gly Arg Pro Tyr His
    210                 215                 220
Ile Arg Ser Ser Thr Ser Ser Lys Glu Ile Val His Thr Phe Glu Thr
225                 230                 235                 240
Thr Val Val Thr Tyr Pro Ser Ala Trp Ser Gln Glu Met Val Ser Leu
                245                 250                 255
Leu Lys Lys Leu Leu Glu Pro Asn Pro Asp Gln Arg Phe Ser Gln Leu
            260                 265                 270
Ser Asp Val Gln Asn Phe Pro Tyr Met Asn Asp Ile Asn Trp Asp Ala
        275                 280                 285
Val Phe Gln Lys Arg Leu Ile Pro Gly Phe Ile Pro Asn Lys Gly Arg
    290                 295                 300
Leu Asn Cys Asp Pro Thr Phe Glu Leu Glu Glu Met Ile Leu Glu Ser
305                 310                 315                 320
Lys Pro Leu His Lys Lys Lys Arg Leu Ala Lys Lys Glu Lys Asp
                325                 330                 335
Met Arg Lys Cys Asp Ser Ser Gln Thr Cys Leu Leu Gln Glu His Leu
            340                 345                 350
Asp Ser Val Gln Lys Glu Phe Ile Ile Phe Asn Arg Glu Lys Val Asn
        355                 360                 365
Arg Asp Phe Asn Lys Arg Gln Pro Asn Leu Ala Leu Glu Gln Thr Lys
    370                 375                 380
Asp Pro Gln Gly Glu Asp Gly Gln Asn Asn Asn Leu
385                 390                 395

<210> SEQ ID NO 12
<211> LENGTH: 1675
<212> TYPE: DNA
<213> ORGANISM: homo sapiens

<400> SEQUENCE: 12
gagcgctaag cggagacgcc cgctggcaag cagatcctgc ctccttccct ggccaaggag      60
ccgcccctcc ggggtagctg tgcgctgggc ggcgctcgga ccccttggca gccgcaggtg     120
cctcccagc ccagcccagc tcagtccagc gcagcccagc ccagcccagc ccggcgctcg     180
cagcctccgc cgcttccggg cagataggtg ccttttcttg ctccttgctc ttggagttct     240
tctcttagtc cctgttccct ggatgaaagc atcgctccga gcctcatggg aggaatgaag     300
gaagaatcga gactagatat ccaactaagg cttcgggaca tgttttgagc gaagatgggt     360
gtttctgccc ggatagtata aatcgaggat ccaggtctgg gcagattcaa ccatgggagc     420
caacacttca agaaaaccac cagtgtttga tgaaaatgaa gatgtcaact ttgaccactt     480
tgaaattttg cgagccattg ggaaaggcag ttttgggaag gtctgcattg tacagaagaa     540
tgataccaag aagatgtacg caatgaagta catgaataaa caaagtgcg tggagcgcaa     600
tgaagtgaga aatgtcttca aggaactcca gatcatgcag gtctggagc acccttcct     660
ggttaatttg tggtattcct tccaagatga ggaagacatg ttcatggtgg tggacctcct     720
gctgggtgga gacctgcgtt atcacctgca acagaacgtc cacttcaagg aagaaacagt     780
gaagctcttc atctgtgagc tggtcatggc cctggactac ctgcagaacc agcgcatcat     840
tcacagggat atgaagcctg acaatatttt acttgacgaa catgggcacg tgcacatcac     900
agattcaac attgctgcga tgctgcccag ggagacacag attaccacca tggctggcac     960
caagccttac atggcacctg agatgttcag ctccagaaaa ggagcaggct attcctttgc    1020
tgttgactgg tggtccctgg gagtgacggc atatgaactg ctgagaggcc ggagaccgta    1080
```

```
tcatattcgc tccagtactt ccagcaagga aattgtacac acgtttgaga cgactgttgt    1140
aacttaccct tctgcctggt cacaggaaat ggtgtcactt cttaaaaagc tactcgaacc    1200
taatccagac caacgatttt ctcagttatc tgatgtccag aacttcccgt atatgaatga    1260
tataaactgg gatgcagttt ttcagaagag gctcattcca ggtttcattc ctaataaagg    1320
caggctgaat tgtgatccta cctttgaact tgaggaaatg attttggagt ccaaacctct    1380
acataagaaa aaaaagcgtc tggcaaagaa ggagaaggat atgaggaaat gcgattcttc    1440
tcagacatgt cttcttcaag agcaccttga ctctgtccag aaggagttca taattttcaa    1500
cagagaaaaa gtaaacaggg actttaacaa aagacaacca aatctagcct tggaacaaac    1560
caaagaccca caagtgacaa atggacaaat ggacacagga ctcagtgaga cttttcagac    1620
ctcgaaagtt tcataaagtg gtcagaatgc cccaggctac ttggataaag ataag         1675
```

HUMAN KINASE PROTEINS AND POLYNUCLEOTIDES ENCODING THE SAME

The present application is a continuation of U.S. application Ser. No. 09/841,683, filed Apr. 24, 2001, now U.S. Pat. No. 6,617,147 which issued on Sep. 9, 2003, which claims the benefit of U.S. Provisional Application Nos. 60/199,499 and 60/201,227 which were filed on Apr. 25, 2000 and May 1, 2000, respectively, each of which are incorporated by reference in their entirety.

1. INTRODUCTION

The present invention relates to the discovery, identification, and characterization of novel human polynucleotides encoding a protein that shares sequence similarity with animal kinases. The invention encompasses the described polynucleotides, host cell expression systems, the encoded proteins, fusion proteins, polypeptides and peptides, antibodies to the encoded proteins and peptides, and genetically engineered animals that either lack or over express the disclosed polynucleotides, antagonists and agonists of the proteins, and other compounds that modulate the expression or activity of the proteins encoded by the disclosed polynucleotides that can be used for diagnosis, drug screening, clinical trial monitoring, the treatment of physiological disorders or diseases, and cosmetic or nutriceutical applications.

2. BACKGROUND OF THE INVENTION

Kinases mediate phosphorylation of a wide variety of proteins and compounds in the cell. Along with phosphatases, kinases are involved in a range of regulatory pathways. Given the physiological importance of kinases, they have been subject to intense scrutiny and are proven drug targets.

3. SUMMARY OF THE INVENTION

The present invention relates to the discovery, identification, and characterization of nucleotides that encode novel human proteins, and the corresponding amino acid sequences of these proteins. The novel human protein (NHP) described for the first time herein shares structural similarity with animal kinases, including, but not limited to, multifunctional calcium-calmodulin dependent protein kinases (SEQ ID NOS:1–3) and to to serine/threonine protein kinases, ribosomal protein kinases, and cAMP-dependant kinases (SEQ ID NOS:4–12). As such, the novel polynucleotides encode a new kinase protein having homologues and orthologs across a range of phyla and species.

The novel human polynucleotides described herein, encode an open reading frame (ORF) encoding a protein of 514 amino acids in length (see SEQ ID NO: 2), 225, 236, 407, and 396 amino acids in length (see SEQ ID NOS: 5, 7, 9, and 11 respectively).

The invention also encompasses agonists and antagonists of the described NHPs, including small molecules, large molecules, mutant NHPs, or portions thereof, that compete with native NHP, peptides, and antibodies, as well as nucleotide sequences that can be used to inhibit the expression of the described NHPs (e.g., antisense and ribozyme molecules, and gene or regulatory sequence replacement constructs) or to enhance the expression of the described NHP polynucleotides (e.g., expression constructs that place the described polynucleotide under the control of a strong promoter system), and transgenic animals that express a NHP transgene, or "knock-outs" (which can be conditional) that do not express a functional NHP. Knock-out mice can be produced in several ways, one of which involves the use of mouse embryonic stem cells ("ES cells") lines that contain gene trap mutations in a murine homolog of at least one of the described NHPs. When the unique NHP sequences described in SEQ ID NOS:1–12 are "knocked-out" they provide a method of identifying phenotypic expression of the particular gene as well as a method of assigning function to previously unknown genes. Additionally, the unique NHP sequences described in SEQ ID NOS:1–12 are useful for the identification of coding sequence and the mapping a unique gene to a particular chromosome.

Further, the present invention also relates to processes for identifying compounds that modulate, i.e., act as agonists or antagonists, of NHP expression and/or NHP activity that utilize purified preparations of the described NHPs and/or NHP product, or cells expressing the same. Such compounds can be used as therapeutic agents for the treatment of any of a wide variety of symptoms associated with biological disorders or imbalances.

4. DESCRIPTION OF THE SEQUENCE LISTING AND FIGURES

The Sequence Listing provides the sequence of the novel human ORFs encoding the described novel human kinase proteins. SEQ ID NO:3 and SEQ ID NO:12 describe full length ORFs and flanking regions.

5. DETAILED DESCRIPTION OF THE INVENTION

The NHP, described for the first time herein, are novel proteins that are widely expressed. SEQ ID NO:1–3 are expressed in, inter alia, human cell lines, and human brain, pituitary, cerebellum, kidney, prostate, testis, thyroid, adrenal gland, pancreas, salivary gland, heart, uterus, cervix, pericardium, fetal kidney and fetal lung cells. SEQ ID NO:1–3 were compiled from human genomic sequence and cDNAs from human trachea and testis cDNA libraries, (Edge Biosystems, Gaithersburg, Md., and Clontech, Palo Alto, Calif.).

The NHPs, described for the first time in SEQ ID NO:4–12 are novel proteins expressed in, inter alia, human cell lines, and human fetal brain, brain, pituitary, cerebellum, spinal cord, trachea, kidney, prostate, testis, thyroid, adrenal gland, pancreas, salivary gland, stomach, adipose, and hypothalamus cells. SEQ ID NO:4–12 were compiled from gene trapped sequences in conjunction with sequences available in GENBANK, and cDNAs from testis, brain, and kidney libraries (Edge Biosystems, Gaithersburg, Md.).

The present invention encompasses the nucleotides presented in the Sequence Listing, host cells expressing such nucleotides, the expression products of such nucleotides, and: (a) nucleotides that encode mammalian homologs of the described polynucleotides, including the specifically described NHPS, and the NHP products; (b) nucleotides that encode one or more portions of the NHPs that correspond to functional domains, and the polypeptide products specified by such nucleotide sequences, including but not limited to the novel regions of any active domain(s); (c) isolated nucleotides that encode mutant versions, engineered or naturally occurring, of the described NHPs in which all or a part of at least one domain is deleted or altered, and the polypeptide products specified by such nucleotide sequences, including but not limited to soluble proteins and peptides in which all or a portion of the signal (or hydrophobic transmembrane) sequence is deleted; (d) nucleotides that encode chimeric fusion proteins containing all or a portion of a coding region of an NHP, or one of its domains (e.g., a receptor or ligand binding domain, accessory protein/self-association domain, etc.) fused to another peptide or polypeptide; or (e) therapeutic or diagnostic derivatives of the described polynucleotides such as oligonucleotides, antisense polynucleotides, ribozymes, dsRNA, or gene therapy constructs comprising a sequence first disclosed in the Sequence Listing. As discussed above, the present invention includes: (a) the human DNA sequences presented in the Sequence Listing (and vectors comprising the same) and additionally contemplates any nucleotide sequence encoding a contiguous NHP open reading frame (ORF) that hybridizes to a complement of a DNA sequence presented in the Sequence Listing under highly stringent conditions, e.g., hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3) and encodes a functionally equivalent gene product. Additionally contemplated are any nucleotide sequences that hybridize to the complement of a DNA sequence that encodes and expresses an amino acid sequence presented in the Sequence Listing under moderately stringent conditions, e.g., washing in 0.2×SSC/0.1% SDS at 42° C. (Ausubel et al., 1989, supra), yet still encodes a functionally equivalent NHP product. Functional equivalents of a NHP include naturally occurring NHPs present in other species and mutant NHPs whether naturally occurring or engineered (by site directed mutagenesis, gene shuffling, directed evolution as described in, for example, U.S. Pat. No. 5,837,458). The invention also includes degenerate nucleic acid variants of the disclosed NHP polynucleotide sequences.

Additionally contemplated are polynucleotides encoding NHP ORFs, or their functional equivalents, encoded by polynucleotide sequences that are about 99, 95, 90, or about 85 percent similar or identical to corresponding regions of the nucleotide sequences of the Sequence Listing (as measured by BLAST sequence comparison analysis using, for example, the GCG sequence analysis package using standard default settings).

The invention also includes nucleic acid molecules, preferably DNA molecules, that hybridize to, and are therefore the complements of, the described NHP nucleotide sequences. Such hybridization conditions may be highly stringent or less highly stringent, as described above. In instances where the nucleic acid molecules are deoxyoligonucleotides ("DNA oligos"), such molecules are generally about 16 to about 100 bases long, or about 20 to about 80, or about 34 to about 45 bases long, or any variation or combination of sizes represented therein that incorporate a contiguous region of sequence first disclosed in the Sequence Listing. Such oligonucleotides can be used in conjunction with the polymerase chain reaction (PCR) to screen libraries, isolate clones, and prepare cloning and sequencing templates, etc.

Alternatively, such NHP oligonucleotides can be used as hybridization probes for screening libraries, and assessing gene expression patterns (particularly using a micro array or high-throughput "chip" format). Additionally, a series of the described NHP oligonucleotide sequences, or the complements thereof, can be used to represent all or a portion of the described NHP sequences. An oligonucleotide or polynucleotide sequence first disclosed in at least a portion of one or more of the sequences of SEQ ID NOS: 1–12 can be used as a hybridization probe in conjunction with a solid support matrix/substrate (resins, beads, membranes, plastics, polymers, metal or metallized substrates, crystalline or polycrystalline substrates, etc.). Of particular note are spatially addressable arrays (i.e., gene chips, microtiter plates, etc.) of oligonucleotides and polynucleotides, or corresponding oligopeptides and polypeptides, wherein at least one of the biopolymers present on the spatially addressable array comprises an oligonucleotide or polynucleotide sequence first disclosed in at least one of the sequences of SEQ ID NOS: 1–12, or an amino acid sequence encoded thereby. Methods for attaching biopolymers to, or synthesizing biopolymers on, solid support matrices, and conducting binding studies thereon are disclosed in, inter alia, U.S. Pat. Nos. 5,700,637, 5,556,752, 5,744,305, 4,631,211, 5,445,934, 5,252,743, 4,713,326, 5,424,186, and 4,689,405 the disclosures of which are herein incorporated by reference in their entirety.

Addressable arrays comprising sequences first disclosed in SEQ ID NOS:1–12 can be used to identify and characterize the temporal and tissue specific expression of a gene. These addressable arrays incorporate oligonucleotide sequences of sufficient length to confer the required specificity, yet be within the limitations of the production technology. The length of these probes is within a range of between about 8 to about 2000 nucleotides. Preferably the probes consist of 60 nucleotides and more preferably 25 nucleotides from the sequences first disclosed in SEQ ID NOS:1–12.

For example, a series of the described oligonucleotide sequences, or the complements thereof, can be used in chip format to represent all or a portion of the described sequences. The oligonucleotides, typically between about 16 to about 40 (or any whole number within the stated range) nucleotides in length can partially overlap each other and/or the sequence may be represented using oligonucleotides that do not overlap. Accordingly, the described polynucleotide sequences shall typically comprise at least about two or three distinct oligonucleotide sequences of at least about 8 nucleotides in length that are each first disclosed in the described Sequence Listing. Such oligonucleotide sequences can begin at any nucleotide present within a sequence in the Sequence Listing and proceed in either a sense (5'-to-3') orientation vis-a-vis the described sequence or in an antisense orientation.

Microarray-based analysis allows the discovery of broad patterns of genetic activity, providing new understanding of gene functions and generating novel and unexpected insight into transcriptional processes and biological mechanisms. The use of addressable arrays comprising sequences first disclosed in SEQ ID NOS:1–12 provides detailed information about transcriptional changes involved in a specific pathway, potentially leading to the identification of novel components or gene functions that manifest themselves as novel phenotypes.

Probes consisting of sequences first disclosed in SEQ ID NOS:1–12 can also be used in the identification, selection and validation of novel molecular targets for drug discovery. The use of these unique sequences permits the direct confirmation of drug targets and recognition of drug dependent changes in gene expression that are modulated through pathways distinct from the drugs intended target. These unique sequences therefore also have utility in defining and monitoring both drug action and toxicity.

As an example of utility, the sequences first disclosed in SEQ ID NOS:1–12 can be utilized in microarrays or other assay formats, to screen collections of genetic material from patients who have a particular medical condition. These investigations can also be carried out using the sequences first disclosed in SEQ ID NOS:1–12 in silico and by comparing previously collected genetic databases and the disclosed sequences using computer software known to those in the art.

Thus the sequences first disclosed in SEQ ID NOS:1–12 can be used to identify mutations associated with a particular disease and also as a diagnostic or prognostic assay.

Although the presently described sequences have been specifically described using nucleotide sequence, it should be appreciated that each of the sequences can uniquely be described using any of a wide variety of additional structural attributes, or combinations thereof. For example, a given sequence can be described by the net composition of the nucleotides present within a given region of the sequence in conjunction with the presence of one or more specific oligonucleotide sequence(s) first disclosed in the SEQ ID NOS: 1–12. Alternatively, a restriction map specifying the relative positions of restriction endonuclease digestion sites, or various palindromic or other specific oligonucleotide sequences can be used to structurally describe a given sequence. Such restriction maps, which are typically generated by widely available computer programs (e.g., the University of Wisconsin GCG sequence analysis package, SEQUENCHER 3.0, Gene Codes Corp., Ann Arbor, Mich., etc.), can optionally be used in conjunction with one or more discrete nucleotide sequence(s) present in the sequence that can be described by the relative position of the sequence relatve to one or more additional sequence(s) or one or more restriction sites present in the disclosed sequence.

For oligonucleotide probes, highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as NHP gene antisense molecules, useful, for example, in NHP gene regulation (for and/or as antisense primers in amplification reactions of NHP gene nucleic acid sequences). With respect to NHP gene regulation, such techniques can be used to regulate biological functions. Further, such sequences may be used as part of ribozyme and/or triple helix sequences that are also useful for NHP gene regulation.

Inhibitory antisense or double stranded oligonucleotides can additionally comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide can also comprise at least one modified sugar moiety selected from the group including but not limited to arabinose, 2-fluoroarabinose, xylulose, and hexose.

In yet another embodiment, the antisense oligonucleotide will comprise at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330). Alternatively, double stranded RNA can be used to disrupt the expression and function of a targeted NHP.

Oligonucleotides of the invention can be synthesized by standard methods known in the art, e.g. by use of an automated DNA synthesizer (such as are commercially available from Biosearch, Applied Biosystems, etc.). As examples, phosphorothioate oligonucleotides can be synthesized by the method of Stein et al. (1988, Nucl. Acids Res. 16:3209), and methylphosphonate oligonucleotides can be prepared by use of controlled pore glass polymer supports (Sarin et al., 1988, Proc. Natl. Acad. Sci. U.S.A. 85:7448–7451), etc.

Low stringency conditions are well known to those of skill in the art, and will vary predictably depending on the specific organisms from which the library and the labeled sequences are derived. For guidance regarding such conditions see, for example, Sambrook et al., 1989, Molecular Cloning, A Laboratory Manual (and periodic updates thereof), Cold Springs Harbor Press, N.Y.; and Ausubel et al., 1989, Current Protocols in Molecular Biology, Green Publishing Associates and Wiley Interscience, N.Y.

Alternatively, suitably labeled NHP nucleotide probes can be used to screen a human genomic library using appropriately stringent conditions or by PCR. The identification and characterization of human genomic clones is helpful for identifying polymorphisms (including, but not limited to, nucleotide repeats, microsatellite alleles, single nucleotide polymorphisms, or coding single nucleotide polymorphisms), determining the genomic structure of a given locus/allele, and designing diagnostic tests. For example, sequences derived from regions adjacent to the intron/exon boundaries of the human gene can be used to design primers for use in amplification assays to detect mutations within the exons, introns, splice sites (e.g., splice acceptor and/or donor sites), etc., that can be used in diagnostics and pharmacogenomics.

Further, a NHP gene homolog can be isolated from nucleic acid from an organism of interest by performing PCR using two degenerate or "wobble" oligonucleotide primer pools designed on the basis of amino acid sequences within the NHP products disclosed herein. The template for the reaction may be total RNA, mRNA, and/or cDNA obtained by reverse transcription of mRNA prepared from human or non-human cell lines or tissue known or suspected to express an allele of a NHP gene.

The PCR product can be subcloned and sequenced to ensure that the amplified sequences represent the sequence of the desired NHP gene. The PCR fragment can then be used to isolate a full length cDNA clone by a variety of methods. For example, the amplified fragment can be labeled and used to screen a cDNA library, such as a bacteriophage cDNA library. Alternatively, the labeled fragment can be used to isolate genomic clones via the screening of a genomic library.

PCR technology can also be used to isolate full length cDNA sequences. For example, RNA can be isolated, following standard procedures, from an appropriate cellular or tissue source (i.e., one known, or suspected, to express a NHP gene). A reverse transcription (RT) reaction can be performed on the RNA using an oligonucleotide primer specific for the most 5' end of the amplified fragment for the priming of first strand synthesis. The resulting RNA/DNA hybrid may then be "tailed" using a standard terminal transferase reaction, the hybrid may be digested with RNase H, and second strand synthesis may then be primed with a complementary primer. Thus, cDNA sequences upstream of the amplified fragment can be isolated. For a review of cloning strategies that can be used, see e.g., Sambrook et al., 1989, supra.

A cDNA encoding a mutant NHP gene can be isolated, for example, by using PCR. In this case, the first cDNA strand may be synthesized by hybridizing an oligo-dT oligonucleotide to mRNA isolated from tissue known or suspected to be expressed in an individual putatively carrying a mutant NHP allele, and by extending the new strand with reverse transcriptase. The second strand of the cDNA is then synthesized using an oligonucleotide that hybridizes specifically to the 5' end of the normal gene. Using these two primers, the product is then amplified via PCR, optionally cloned into a suitable vector, and subjected to DNA sequence analysis through methods well known to those of skill in the art. By comparing the DNA sequence of the mutant NHP allele to that of a corresponding normal NHP allele, the mutation(s) responsible for the loss or alteration of function of the mutant NHP gene product can be ascertained.

Alternatively, a genomic library can be constructed using DNA obtained from an individual suspected of or known to carry a mutant NHP allele (e.g., a person manifesting a NHP-associated phenotype such as, for example, obesity, high blood pressure,immune disorders, connective tissue disorders, infertility, etc.), or a cDNA library can be constructed using RNA from a tissue known, or suspected, to express a mutant NHP allele. A normal NHP gene, or any suitable fragment thereof, can then be labeled and used as a probe to identify the corresponding mutant NHP allele in such libraries. Clones containing mutant NHP gene sequences can then be purified and subjected to sequence analysis according to methods well known to those skilled in the art.

Additionally, an expression library can be constructed utilizing cDNA synthesized from, for example, RNA isolated from a tissue known, or suspected, to express a mutant NHP allele in an individual suspected of or known to carry such a mutant allele. In this manner, gene products made by the putatively mutant tissue can be expressed and screened using standard antibody screening techniques in conjunction with antibodies raised against a normal NHP product, as described below. (For screening techniques, see, for example, Harlow, E. and Lane, eds., 1988, "Antibodies: A Laboratory Manual", Cold Spring Harbor Press, Cold Spring Harbor, N.Y.).

Additionally, screening can be accomplished by screening with labeled NHP fusion proteins, such as, for example, alkaline phosphatase-NHP or NHP-alkaline phosphatase fusion proteins. In cases where a NHP mutation results in an expressed gene product with altered function (e.g., as a result of a missense or a frameshift mutation), polyclonal antibodies to a NHP are likely to cross-react with a corresponding mutant NHP gene product. Library clones detected via their reaction with such labeled antibodies can be purified and subjected to sequence analysis according to methods well known in the art.

The invention also encompasses (a) DNA vectors that contain any of the foregoing NHP coding sequences and/or their complements (i.e., antisense); (b) DNA expression vectors that contain any of the foregoing NHP coding sequences operatively associated with a regulatory element that directs the expression of the coding sequences (for example, baculo virus as described in U.S. Pat. No. 5,869, 336 herein incorporated by reference); (c) genetically engineered host cells that contain any of the foregoing NHP coding sequences operatively associated with a regulatory element that directs the expression of the coding sequences in the host cell; and (d) genetically engineered host cells that express an endogenous NHP gene under the control of an exogenously introduced regulatory element (i.e., gene activation). As used herein, regulatory elements include, but are not limited to, inducible and non-inducible promoters, enhancers, operators and other elements known to those skilled in the art that drive and regulate expression. Such regulatory elements include but are not limited to the cytomegalovirus (hCMV) immediate early gene, regulatable, viral elements (particularly retroviral LTR promoters), the early or late promoters of SV40 adenovirus, the lac system, the trp system, the TAC system, the TRC system, the major operator and promoter regions of phage lambda, the control regions of fd coat protein, the promoter for 3-phosphoglycerate kinase (PGK), the promoters of acid phosphatase, and the promoters of the yeast α-mating factors.

The present invention also encompasses antibodies and anti-idiotypic antibodies (including Fab fragments), antagonists and agonists of the NHP, as well as compounds or nucleotide constructs that inhibit expression of a NHP gene (transcription factor inhibitors, antisense and ribozyme molecules, or gene or regulatory sequence replacement constructs), or promote the expression of a NHP ( e.g., expression constructs in which NHP coding sequences are operatively associated with expression control elements such as promoters, promoter/enhancers, etc.).

The NHPs or NHP peptides, NHP fusion proteins, NHP nucleotide sequences, antibodies, antagonists and agonists can be useful for the detection of mutant NHPs or inappropriately expressed NHPs for the diagnosis of disease. The NHP proteins or peptides, NHP fusion proteins, NHP nucleotide sequences, host cell expression systems, antibodies, antagonists, agonists and genetically engineered cells and animals can be used for screening for drugs (or high throughput screening of combinatorial libraries) effective in the treatment of the symptomatic or phenotypic manifestations of perturbing the normal function of NHP in the body. The use of engineered host cells and/or animals may offer an advantage in that such systems allow not only for the identification of compounds that bind to the endogenous receptor for an NHP, but can also identify compounds that trigger NHP-mediated activities or pathways.

Finally, the NHP products can be used as therapeutics. For example, soluble derivatives such as NHP peptides/domains corresponding to NHPs, NHP fusion protein products (especially NHP-Ig fusion proteins, i.e., fusions of a NHP, or a domain of a NHP, to an IgFc), NHP antibodies and anti-idiotypic antibodies (including Fab fragments), antagonists or agonists (including compounds that modulate or act on downstream targets in a NHP-mediated pathway) can be used to directly treat diseases or disorders. For instance, the administration of an effective amount of soluble NHP, or a NHP-IgFc fusion protein or an anti-idiotypic antibody. (or its Fab) that mimics the NHP could activate or effectively antagonize the endogenous NHP receptor. Nucleotide constructs encoding such NHP products can be used to genetically engineer host cells to express such products in vivo; these genetically engineered cells function as "bioreactors" in the body delivering a continuous supply of a NHP, a NHP peptide, or a NHP fusion protein to the body. Nucleotide constructs encoding functional NHPs, mutant NHPs, as well as antisense and ribozyme molecules can also be used in "gene therapy" approaches for the modulation of NHP expression. Thus, the invention also encompasses pharmaceutical formulations and methods for treating biological disorders.

Various aspects of the invention are described in greater detail in the subsections below.

5.1 THE NHP SEQUENCES

The cDNA sequences and the corresponding deduced amino acid sequences of the described NHPs are presented in the Sequence Listing. SEQ ID NOS:1–3 describe sequences that are similar to multifunctional calcium-calmodulin dependent protein kinases. These NHP nucleotide sequences were obtained from a human cDNA library using probes and/or primers generated from human genomic sequence. SEQ ID NO:3 describes a NHP ORF as well as flanking regions.

SEQ ID NOS:4–12 describe sequences that are similar to serine/threonine protein kinases, ribosomal protein kinases, and cAMP-dependant kinases. Expression analysis has provided evidence that the described NHPs can be expressed in human tissues as well as gene trapped human cells. In addition to serine/threonine kinases, the described NHPs also share significant similarity to a range of additional kinase families from a variety of phyla and species.

A translationally silent polymorphism involving possible C-or-G transversion at the sequence position corresponding to, for example, nucleotide 9 of SED ID NO:4. SEQ ID NO:12 describes a NHP ORF as well as flanking regions.

An additional application of the described novel human polynucleotide sequences is their use in the molecular mutagenesis/evolution of proteins that are at least partially encoded by the described novel sequences using, for example, polynucleotide shuffling or related methodologies. Such approaches are described in U.S. Pat. Nos. 5,830,721 and 5,837,458 which are herein incorporated by reference in their entirety.

NHP gene products can also be expressed in transgenic animals. Animals of any species, including, but not limited to, worms, mice, rats, rabbits, guinea pigs, pigs, micro-pigs, birds, goats, and non-human primates, e.g., baboons, monkeys, and chimpanzees may be used to generate NHP transgenic animals.

Any technique known in the art may be used to introduce a NHP transgene into animals to produce the founder lines of transgenic animals. Such techniques include, but are not limited to pronuclear microinjection (Hoppe, P. C. and Wagner, T. E., 1989, U.S. Pat. No. 4,873,191); retrovirus mediated gene transfer into germ lines (Van der Putten et al., 1985, Proc. Natl. Acad. Sci., USA 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety.

The present invention provides for transgenic animals that carry the NHP transgene in all their cells, as well as animals which carry the transgene in some, but not all their cells, i.e., mosaic animals or somatic cell transgenic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al., 1992, Proc. Natl. Acad. Sci. USA 89:6232–6236. The regulatory sequences required for such a cell-type specific activation will depend upon the particular cell type of interest, and will be apparent to those of skill in the art.

When it is desired that a NHP transgene be integrated into the chromosomal site of the endogenous NHP gene, gene targeting is preferred. Briefly, when such a technique is to be utilized, vectors containing some nucleotide sequences homologous to the endogenous NHP gene are designed for the purpose of integrating, via homologous recombination with chromosomal sequences, into and disrupting the function of the nucleotide sequence of the endogenous NHP gene ( i.e., "knockout" animals).

The transgene can also be selectively introduced into a particular cell type, thus inactivating the endogenous NHP gene in only that cell type, by following, for example, the teaching of Gu et al., 1994, Science, 265:103–106. The regulatory sequences required for such a cell-type specific inactivation will depend upon the particular cell type of interest, and will be apparent to those of skill in the art.

Once transgenic animals have been generated, the expression of the recombinant NHP gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques which include but are not limited to Northern blot analysis of tissue samples obtained from the animal, in situ hybridization analysis, and RT-PCR. Samples of NHP gene-expressing tissue, may also be evaluated immunocytochemically using antibodies specific for the NHP transgene product.

5.2 NHPS AND NHP POLYPEPTIDES

NHPs, polypeptides, peptide fragments, mutated, truncated, or deleted forms of the NHPs, and/or NHP fusion proteins can be prepared for a variety of uses. These uses include but are not limited to the generation of antibodies, as reagents in diagnostic assays, the identification of other cellular gene products related to a NHP, as reagents in assays for screening for compounds that can be used as pharmaceutical reagents useful in the therapeutic treatment of mental, biological, or medical disorders and diseases. Given the similarity information and expression data, the described NHPs can be targeted (by drugs, oligos, antibodies, etc,) in order to treat disease, or to therapeutically augment the efficacy of, for example, chemotherapeutic agents used in the treatment of breast or prostate cancer.

The Sequence Listing discloses the amino acid sequences encoded by the described NHP polynucleotides. The NHPs typically display have initiator methionines in DNA sequence contexts consistent with a translation initiation site.

The NHP amino acid sequences of the invention include the amino acid sequence presented in the Sequence Listing as well as analogues and derivatives thereof. Further, corresponding NHP homologues from other species are encompassed by the invention. In fact, any NHP protein encoded by the NHP nucleotide sequences described above are within the scope of the invention, as are any novel polynucleotide sequences encoding all or any novel portion of an amino acid sequence presented in the Sequence Listing. The degenerate nature of the genetic code is well known, and, accordingly, each amino acid presented in the Sequence Listing, is generically representative of the well known nucleic acid "triplet" codon, or in many cases codons, that can encode the amino acid. As such, as contemplated herein, the amino acid sequences presented in the Sequence Listing, when taken together with the genetic code (see, for example, Table 4-1 at page 109 of "Molecular Cell Biology", 1986, J. Darnell et al. eds., Scientific American Books, New York, N.Y., herein incorporated by reference) are generically representative of all the various permutations and combinations of nucleic acid sequences that can encode such amino acid sequences.

The invention also encompasses proteins that are functionally equivalent to the NHPs encoded by the presently described nucleotide sequences as judged by any of a number of criteria, including, but not limited to, the ability to bind and cleave a substrate of a NHP, or the ability to effect an identical or complementary downstream pathway, or a change in cellular metabolism (e.g., proteolytic activity, ion flux, tyrosine phosphorylation, etc.). Such functionally equivalent NHP proteins include, but are not limited to, additions or substitutions of amino acid residues within the amino acid sequence encoded by the NHP nucleotide sequences described above, but which result in a silent change, thus producing a functionally equivalent gene product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

A variety of host-expression vector systems can be used to express the NHP nucleotide sequences of the invention. Where, as in the present instance, the NHP peptide or polypeptide is thought to be membrane protein, the hydrophobic regions of the protein can be excised and the resulting soluble peptide or polypeptide can be recovered from the culture media. Such expression systems also encompass engineered host cells that express a NHP, or functional equivalent, in situ. Purification or enrichment of a NHP from such expression systems can be accomplished using appropriate detergents and lipid micelles and methods well known to those skilled in the art. However, such engineered host cells themselves may be used in situations where it is important not only to retain the structural and functional characteristics of the NHP, but to assess biological activity, e.g., in drug screening assays.

The expression systems that may be used for purposes of the invention include but are not limited to microorganisms such as bacteria (e.g., *E. coli, B. subtilis*) transformed with recombinant bacteriophage DNA, plasmid DNA or cosmid DNA expression vectors containing NHP nucleotide sequences; yeast (e.g., *Saccharomyces, Pichia*) transformed with recombinant yeast expression vectors containing NHP nucleotide sequences; insect cell systems infected with recombinant virus expression vectors (e.g., baculovirus) containing NHP sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing NHP nucleotide sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the NHP product being expressed. For example, when a large quantity of such a protein is to be produced for the generation of pharmaceutical compositions of or containing NHP, or for raising antibodies to a NHP, vectors that direct the expression of high levels of fusion protein products that are readily purified may be desirable. Such vectors include, but are not limited to, the *E. coli* expression vector pUR278 (Ruther et al., 1983, EMBO J. 2:1791), in which a NHP coding sequence may be ligated individually into the vector in frame with the lacZ coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. PGEX vectors (Pharmacia or American Type Culture Collection) can also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned target gene product can be released from the GST moiety.

In an insect system, *Autographa californica* nuclear polyhidrosis virus (AcNPV) is used as a vector to express foreign genes. The virus grows in *Spodoptera frugiperda* cells. A NHP coding sequence may be cloned individually into non-essential regions (for example the polyhedrin gene) of the virus and placed under control of an AcNPV promoter (for example the polyhedrin promoter). Successful insertion of NHP coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted sequence is expressed (e.g., see Smith et al., 1983, J. Virol. 46:584; Smith, U.S. Pat. No. 4,215,051).

In mammalian host cells, a number of viral-based expression systems may be utilized. In cases where an adenovirus is used as an expression vector, the NHP nucleotide sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing a NHP product in infected hosts (e.g., See Logan & Shenk, 1984, Proc. Natl. Acad. Sci. USA 81:3655–3659). Specific initiation signals may also be required for efficient translation of inserted NHP nucleotide sequences. These signals include the ATG initiation codon and adjacent sequences. In cases where an entire NHP gene or cDNA, including its own initiation codon and adjacent sequences, is inserted into the appropriate expression vector, no additional translational control signals may be needed. However, in cases where only a portion of a NHP coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (See Bitter et al., 1987, Methods in Enzymol. 153:516–544).

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, VERO, BHK, HeLa, COS, MDCK, 293, 3T3, WI38, and in particular, human cell lines.

For long-term, high-yield production of recombinant proteins, stable expression is preferred. For example, cell lines which stably express the NHP sequences described above can be engineered. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the NHP product. Such engineered cell lines may be particularly useful in screening and evaluation of compounds that affect the endogenous activity of the NHP product.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy,et al., 1980, Cell 22:817) genes can be employed in tk$^-$, hgprt$^-$ or aprt$^-$ cells, respectively. Also, antimetabolite resistance can be used as the basis of selection for the following genes: dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

Alternatively, any fusion protein can be readily purified by utilizing an antibody specific for the fusion protein being expressed. For example, a system described by Janknecht et al. allows for the ready purification of non-denatured fusion proteins expressed in human cell lines (Janknecht, et al., 1991, Proc. Natl. Acad. Sci. USA 88:8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$ nitriloacetic acid-agarose columns and histidine-tagged proteins are selectively eluted with imidazole-containing buffers.

Also encompassed by the present invention are fusion proteins that direct the NHP to a target organ and/or facilitate transport across the membrane into the cytosol. Conjugation of NHPs to antibody molecules or their Fab fragments could be used to target cells bearing a particular epitope. Attaching the appropriate signal sequence to the NHP would also transport the NHP to the desired location within the cell. Alternatively targeting of NHP or its nucleic acid sequence might be achieved using liposome or lipid complex based delivery systems. Such technologies are described in *Liposomes: A Practical Approach,* New, RRC ed., Oxford University Press, New York and in U.S. Pat. Nos. 4,594,595, 5,459,127, 5,948,767 and 6,110,490 and their respective disclosures which are herein incorporated by reference in their entirety. Additionally embodied are novel protein constructs engineered in such a way that they facilitate transport of the NHP to the target site or desired organ. This goal may be achieved by coupling of the NHP to a cytokine or other ligand that provides targeting specificity, and/or to a protein transducing domain (see generally U.S. applications Ser. No. 60/111,701 and 60/056,713, both of which are herein incorporated by reference, for examples of such transducing sequences) to facilitate passage across cellular membranes if needed and can optionally be engineered to include nuclear localization sequences when desired.

5.3 ANTIBODIES TO NHP PRODUCTS

Antibodies that specifically recognize one or more epitopes of a NHP, or epitopes of conserved variants of a NHP, or peptide fragments of a NHP are also encompassed by the invention. Such antibodies include but are not limited to polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above.

The antibodies of the invention may be used, for example, in the detection of NHP in a biological sample and may, therefore, be utilized as part of a diagnostic or prognostic technique whereby patients may be tested for abnormal amounts of NHP. Such antibodies may also be utilized in conjunction with, for example, compound screening schemes for the evaluation of the effect of test compounds on expression and/or activity of a NHP gene product. Additionally, such antibodies can be used in conjunction gene therapy to, for example, evaluate the normal and/or engineered NHP-expressing cells prior to their introduction into the patient. Such antibodies may additionally be used as a method for the inhibition of abnormal NHP activity. Thus, such antibodies may, therefore, be utilized as part of treatment methods.

For the production of antibodies, various host animals may be immunized by injection with a NHP, an NHP peptide (e.g., one corresponding to a functional domain of an NHP), truncated NHP polypeptides (NHP in which one or more domains have been deleted), functional equivalents of the NHP or mutated variant of the NHP. Such host animals may include but are not limited to pigs, rabbits, mice, goats, and rats, to name but a few. Various adjuvants may be used to increase the immunological response, depending on the host species, including but not limited to Freund's adjuvant (complete and incomplete), mineral salts such as aluminum hydroxide or aluminum phosphate, surface active substances such as lysolecithin, pluronic polyols, polyanions, peptides, oil emulsions, and potentially useful human adjuvants such as BCG (bacille Calmette-Guerin) and *Corynebacterium parvum*. Alternatively, the immune response could be enhanced by combination and or coupling with molecules such as keyhole limpet hemocyanin, tetanus toxoid, diptheria toxoid, ovalbumin, cholera toxin or fragments thereof. Polyclonal antibodies are heterogeneous populations of antibody molecules derived from the sera of the immunized animals.

Monoclonal antibodies, which are homogeneous populations of antibodies to a particular antigen, can be obtained by any technique which provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mabs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region. Such technologies are described in U.S. Pat. Nos. 6,075,181 and 5,877,397 and their respective disclosures which are herein incorporated by reference in their entirety. Also encompassed by the present invention is the use of fully humanized monoclonal antibodies as described in U.S. Pat. No. 6,150,584 and respective disclosures which are herein incorporated by reference in their entirety.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 341:544–546) can be adapted to produce single chain antibodies against NHP gene products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include, but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity.

Antibodies to a NHP can, in turn, be utilized to generate anti-idiotype antibodies that "mimic" a given NHP, using techniques well known to those skilled in the art. (See, e.g., Greenspan & Bona, 1993, FASEB J 7(5):437–444; and Nissinoff, 1991, J. Immunol. 147(8):2429–2438). For example antibodies which bind to a NHP domain and competitively inhibit the binding of NHP to its cognate receptor can be used to generate anti-idiotypes that "mimic" the NHP and, therefore, bind and activate or neutralize a receptor. Such anti-idiotypic antibodies or Fab fragments of such anti-idiotypes can be used in therapeutic regimens involving a NHP mediated pathway.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims. All cited publications, patents, and patent applications are herein incorporated by reference in their entirety.

What is claimed is:

1. An isolated nucleic acid molecule comprising a nucleotide sequence that:
   (a) encodes the amino acid sequence shown in SEQ ID NO: 9; and
   (b) hybridizes under stringent conditions to the nucleotide sequence of SEQ ID NO: 8 or the complement thereof.

2. An isolated nucleic acid molecule comprising a nucleotide sequence encoding the amino acid sequence shown in SEQ ID NO:9.

3. An isolated nucleic acid molecule comprising the nucleotide sequence shown in SEQ ID NO:8.

4. A recombinant expression vector comprising a nucleotide sequence encoding the amino acid sequence shown in SEQ ID NO:9.

5. The recombinant expression vector of claim 4 wherein said nucleotide sequence is that shown in SEQ ID NO:8.

6. A host cell comprising the vector of claim 4.

7. A host cell comprising the vector of claim 5.

* * * * *